United States Patent
Broderick et al.

(10) Patent No.: US 10,550,049 B2
(45) Date of Patent: Feb. 4, 2020

(54) HYDROCARBON CONVERSION PROCESSES USING NON-CYCLIC AMIDE AND THIOAMIDE BASED IONIC LIQUIDS

(71) Applicant: UOP LLC, Des Plaines, IL (US)

(72) Inventors: Erin M. Broderick, Arlington Heights, IL (US); Avram M. Buchbinder, Chicago, IL (US); Alakananda Bhattacharyya, Glen Ellyn, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/867,403

(22) Filed: Jan. 10, 2018

(65) Prior Publication Data

US 2018/0127334 A1 May 10, 2018

Related U.S. Application Data

(63) Continuation of application No. PCT/US2016/040969, filed on Jul. 5, 2016.

(60) Provisional application No. 62/190,944, filed on Jul. 10, 2015.

(51) Int. Cl.
*C07C 2/60* (2006.01)
*B01J 31/02* (2006.01)
*B01J 31/40* (2006.01)

(52) U.S. Cl.
CPC .............. *C07C 2/60* (2013.01); *B01J 31/0285* (2013.01); *B01J 31/40* (2013.01); *C07C 2531/02* (2013.01)

(58) Field of Classification Search
CPC .......................... B01J 31/0279; B01J 31/0285
See application file for complete search history.

(56) References Cited

U.S. PATENT DOCUMENTS

| | | |
|---|---|---|
| 3,155,642 A | 11/1964 | Duck et al. |
| 3,170,904 A | 2/1965 | Ueda et al. |
| 3,170,906 A | 2/1965 | Ueda et al. |
| 3,457,321 A | 7/1969 | Hambling et al. |
| 3,483,268 A | 12/1969 | Hambling et al. |
| 3,483,269 A | 12/1969 | Magoon et al. |
| 3,505,425 A | 4/1970 | Jones et al. |
| 3,562,351 A | 2/1971 | Mertzweiller et al. |

(Continued)

FOREIGN PATENT DOCUMENTS

| | | |
|---|---|---|
| CN | 1798731 A | 7/2006 |
| CN | 1944439 A | 4/2007 |

(Continued)

OTHER PUBLICATIONS

Coleman et al. Liquid Coordination Complexes Formed by the Heterolytic Cleavage of Metal Halides. Angewandte Chemie International Edition, 2013, 52. 12582-12586 (Year: 2013).*

(Continued)

*Primary Examiner* — Philip Y Louie
*Assistant Examiner* — Alyssa L Cepluch (57) ABSTRACT

A hydrocarbon conversion process is described. The process involves contacting a hydrocarbon feed with a non-cyclic amide or thioamide based ionic liquid catalyst in a reaction zone under reaction conditions to form a mixture comprising reaction products, and the non-cyclic amide or thioamide based ionic liquid catalyst. Typical hydrocarbon conversion processes include alkylation, oligomerization, isomerization, disproportionation, and reverse disproportionation.

19 Claims, 1 Drawing Sheet

(56) References Cited

U.S. PATENT DOCUMENTS

| | | | |
|---|---|---|---|
| 3,592,869 A | 7/1971 | Cannell | |
| 3,644,564 A | 2/1972 | van Zwet et al. | |
| 3,663,451 A | 5/1972 | Hill | |
| 3,679,772 A | 7/1972 | Yoo | |
| 3,697,617 A | 10/1972 | Yoo et al. | |
| 3,755,490 A | 8/1973 | Yoo et al. | |
| 3,914,330 A * | 10/1975 | Hughes | C07C 6/10 208/134 |
| 3,954,668 A | 5/1976 | Yoo et al. | |
| 3,981,941 A | 9/1976 | Butter | |
| 4,520,221 A | 5/1985 | Hsia Chen | |
| 4,547,613 A | 10/1985 | Garwood et al. | |
| 4,642,404 A | 2/1987 | Shihabi | |
| 4,757,042 A | 7/1988 | Threlkel | |
| 4,764,440 A | 8/1988 | Jones et al. | |
| 5,104,840 A | 4/1992 | Chauvin et al. | |
| 5,284,989 A | 2/1994 | Apelian et al. | |
| 5,824,832 A | 10/1998 | Sherif et al. | |
| 5,895,830 A | 4/1999 | Stine et al. | |
| 6,686,511 B2 * | 2/2004 | Miller | C10G 50/02 208/18 |
| 7,053,261 B2 | 5/2006 | Herbst et al. | |
| 7,544,813 B2 | 6/2009 | Harmer et al. | |
| 8,070,939 B2 * | 12/2011 | Hommeltoft | C10G 29/205 208/133 |
| 8,613,865 B2 | 12/2013 | Choi et al. | |
| 9,096,480 B2 | 8/2015 | Smith et al. | |
| 9,096,481 B2 | 8/2015 | Smith et al. | |
| 9,096,482 B2 | 8/2015 | Smith et al. | |
| 9,096,485 B2 | 8/2015 | Smith et al. | |
| 9,102,577 B2 | 8/2015 | Smith et al. | |
| 9,102,578 B2 | 8/2015 | Smith et al. | |
| 9,126,881 B2 | 9/2015 | Smith et al. | |
| 2004/0059173 A1 | 3/2004 | Houzvicka et al. | |
| 2008/0021254 A1 * | 1/2008 | Schmidt | H02S 20/00 585/702 |
| 2010/0224063 A1 * | 9/2010 | Choi | B01D 53/1475 95/236 |
| 2011/0229401 A1 | 9/2011 | Dai et al. | |
| 2013/0001092 A1 * | 1/2013 | Abbott | C07C 233/05 205/238 |
| 2013/0012699 A1 | 1/2013 | Choi et al. | |
| 2014/0171710 A1 * | 6/2014 | Mahieux | C07C 7/14883 585/448 |
| 2015/0005540 A1 | 1/2015 | Smith et al. | |
| 2017/0203286 A1 * | 7/2017 | Uppara | C07C 67/293 |

FOREIGN PATENT DOCUMENTS

| | | |
|---|---|---|
| CN | 101234994 A | 8/2008 |
| CN | 101941986 A | 1/2011 |
| CN | 102146165 A | 8/2011 |
| CN | 103071367 A | 5/2013 |
| GB | 1123474 | 8/1968 |
| KR | 1071774 B1 | 10/2011 |
| WO | 2010074835 A2 | 7/2010 |

OTHER PUBLICATIONS

Guo, "Oxa-Michael addition catalyzed by amide-based acidic ionic liquids", Cuihua Xuebao (2011), 32(1), 162-165. | Language: Chinese.

Zhang, "Characterizing the Structural Properties of N,N-Dimethylformamide-Based Ionic Liquid: Density-Functional Study", J. Phys. Chem. B 2007, 111, 11016-11020.

Search Report dated Oct. 20, 2016 for corresponding PCT Appl. No. PCT/US2016/040969.

Cook, Denys, Protonated Carbonyl Groups, IV. N, N-Dimethylacetamide Salts, Canadian Journal of Chemistry, vol. 42, 1964.

W.D. Kumler, Structure of Salts of N, N-Dimethylacetamide and N, N-Di-(n)butylacetamide, J. Am. Chem. Soc., 1961, vol. 83, pp. 4983-4985.

E. Spinner, The vibration spectra and structures of the hydrochloride or urea, thiourea and acetamide. The basic properties of amides and thioamides, Spectrochimica Acta, 1959, pp. 95-109.

O.D. Bonner, et al., The Raman spectra of the hydrochloride salts of N-methylacetamide, Spectrochimica Acta, 1966, vol. 22, pp. 1125-1129, Pergamon Press, Ltd.

Zaleska, Barbara et al., Perhydropyrimidinylium and 1,3-diazepinylium salts as potential ionic liquids, ISSN 1424-6376, ARKIVOC 2007 (iv) 64-74.

* cited by examiner

HYDROCARBON CONVERSION PROCESSES USING NON-CYCLIC AMIDE AND THIOAMIDE BASED IONIC LIQUIDS

CROSS-REFERENCE TO RELATED APPLICATIONS

This application is a Continuation of International Application No. PCT/US2016/040969 filed Jul. 5, 2016 which application claims benefit of U.S. Provisional Application No. 62/190,944 filed Jul. 10, 2015, the contents of which cited applications are hereby incorporated by reference in their entirety.

BACKGROUND OF THE INVENTION

There are a variety of hydrocarbon conversion processes, and these processes utilize different catalysts.

Alkylation is typically used to combine light olefins, for example mixtures of alkenes such as propylene and butylene, with isobutane to produce a relatively high-octane branched-chain paraffinic hydrocarbon fuel, including isoheptane and isooctane. Similarly, an alkylation reaction can be performed using an aromatic compound such as benzene in place of the isobutane. When using benzene, the product resulting from the alkylation reaction is an alkylbenzene (e.g. ethylbenzene, cumene, dodecylbenzene, etc.).

The alkylation of paraffins with olefins for the production of alkylate for gasoline can use a variety of catalysts. The choice of catalyst depends on the end product a producer desires. Typical alkylation catalysts include concentrated sulfuric acid or hydrofluoric acid. However, sulfuric acid and hydrofluoric acid are hazardous and corrosive, and their use in industrial processes requires a variety of environmental controls.

Solid catalysts are also used for alkylation. However, solid catalysts are generally rapidly deactivated by the presence of water, which may be present in the feed.

Processes for the oligomerization of light olefins (e.g. ethylene, propylene, and butylene) to produce higher carbon number olefin products (e.g. $C_{6+}$ olefins) are well known. Oligomerization processes have been employed to produce high quality motor fuel components as well as petrochemicals from ethylene, propylene, and butylene. These oligomerization processes are also referred to as catalytic condensation and polymerization, with the resulting motor fuel often referred to as polymer gasoline. In the refining area, methods have been continually sought to improve the octane number of the gasoline boiling range oligomerization products. This octane enhancement is generally realized through the improvement of the oligomerization reaction selectivity to enhance the representation of high octane blending components (e.g., branched olefins) in the product slate. The ability of the process to better target specific carbon number species is also a primary consideration when highly purified chemical grade products are desired. In any case, the enrichment of product slate to the targeted species, in addition to providing a higher quality and quantity of useable products, also benefits catalyst life. This is due to the reduction in non-selective heavy oligomers that condense into coke which ultimately covers the catalyst.

Known catalysts for effecting the oligomerization reaction include heterogeneous catalysts such as solid acids and homogeneous catalysts, in particular boron trifluoride as described, for example, in U.S. Pat. No. 3,981,941. Other catalysts fall within the description of mild protonic acids, generally having a Hammett acidity function of less than −5.0. Particularly preferred among these are solid phosphoric acid (SPA) catalysts having as a principal ingredient an acid of phosphorous such as ortho, pyro, or tetraphosphoric acid. Details of SPA catalysts are provided in the prior art, for example in U.S. Pat. No. 5,895,830. The use of zeolites as oligomerization catalysts is also described, along with various catalyst treatment methods designed to improve performance in U.S. Pat. Nos. 4,547,613, 4,520,221, 4,642,404, and 5,284,989, for example. Another type of catalyst which may be employed comprises a supported metal compound, as described in U.S. Pat. Nos. 3,562,351, 3,483,269, 3,592,869 3,644,564, 3,679,772, 3,697,617, 3,663,451, 3,755,490, 3,954,668, 3,170,904, 3,170,906. Unsupported metal catalysts are described in, U.S. Pat. Nos. 3,155,642, 3,155,642, 3,457,321, 3,483,268, and 3,505,425, and British Patent 1,123,474. U.S. Pat. No. 4,757,042 describes a catalyst comprising a complex of nickel or palladium, certain fluoro-organo sulfur ligands and an organo-metallic reducing agent.

The disproportionation of paraffins (e.g., isopentane ($iC_5$)) involves reacting two moles of hydrocarbon to form one mole each of two different products, one having a carbon count greater than the starting material and the other having a carbon count less than the starting material. The total number of moles in the system remains the same throughout the process, but the products have different carbon counts from the reactants.

Suitable catalysts include, but are not limited to, HF, sulfated zirconias, $AlCl_3/SiO_2$, zeolites, ionic solids, platinum on chlorided $Al_2O_3/Ga_2O_3$ supports, supported ionic liquids, $Pt/W/Al_2O_3$, $HF/TiF_4$, or combinations thereof.

Isomerization of linear paraffins to their branched isomers increases their octane number and thus their value to a refiner. Isomerization processes involve reacting one mole of a hydrocarbon (e.g., normal pentane) to form one mole of an isomer of that specific hydrocarbon (e.g., isopentane). The total number of moles remains the same throughout this process, and the product has the same number of carbons as the reactant.

Current isomerization processes use chlorided alumina, sulfated zirconia, or zeolites in conjunction with platinum. Process temperatures range from about 120° C. for chlorided alumina up to about 260° C. for zeolite type catalysts. These reactions are run at temperatures which allow the feed to reach equilibrium. At lower temperatures, the equilibrium favors the branched isomers possessing the higher octane number.

Acidic ionic liquids can be used as an alternative to the commonly used strong acid catalysts in hydrocarbon conversion processes. Ionic liquids are catalysts that can be used in a variety of catalytic reactions, including the alkylation of paraffins with olefins. Ionic liquids are salts comprised of cations and anions which typically melt below about 100° C.

Ionic liquids are essentially salts in a liquid state, and are described in U.S. Pat. Nos. 4,764,440, 5,104,840, and 5,824,832. The properties vary extensively for different ionic liquids, and the use of ionic liquids depends on the properties of a given ionic liquid. Depending on the organic cation of the ionic liquid and the anion, the ionic liquid can have very different properties.

Although ionic liquid catalysts can be very active, alkylation reactions need to be run at low temperatures, typically between −10° C. to 30° C., to maximize the alkylate quality. This requires cooling the reactor and reactor feeds, which adds substantial cost to an alkylation process utilizing ionic liquids in the form of additional equipment and energy. The most common ionic liquid catalyst precursors for alkylation include imidazolium, or pyridinium-based cations coupled with the chloroaluminate anion ($Al_2Cl_7^-$).

Isomerization processes utilizing ionic liquid catalysts have been developed, such as, US 2004/059173, and U.S. Pat. No. 7,053,261, for example.

Ionic liquids provide advantages over other catalysts, including being less corrosive than catalysts like HF, and being non-volatile.

However, the cost of ionic liquids has limited the widespread adoption of ionic liquids.

There is a need for lower cost ionic liquids for use in a variety of hydrocarbon conversion processes.

SUMMARY OF THE INVENTION

One aspect of the present invention is a hydrocarbon conversion process. In one embodiment, the process involves contacting a hydrocarbon feed with a non-cyclic amide or thioamide based ionic liquid catalyst in a reaction zone under reaction conditions to form a mixture comprising reaction products, and the non-cyclic amide or thioamide based ionic liquid catalyst.

DETAILED DESCRIPTION OF THE INVENTION

Figure 1:
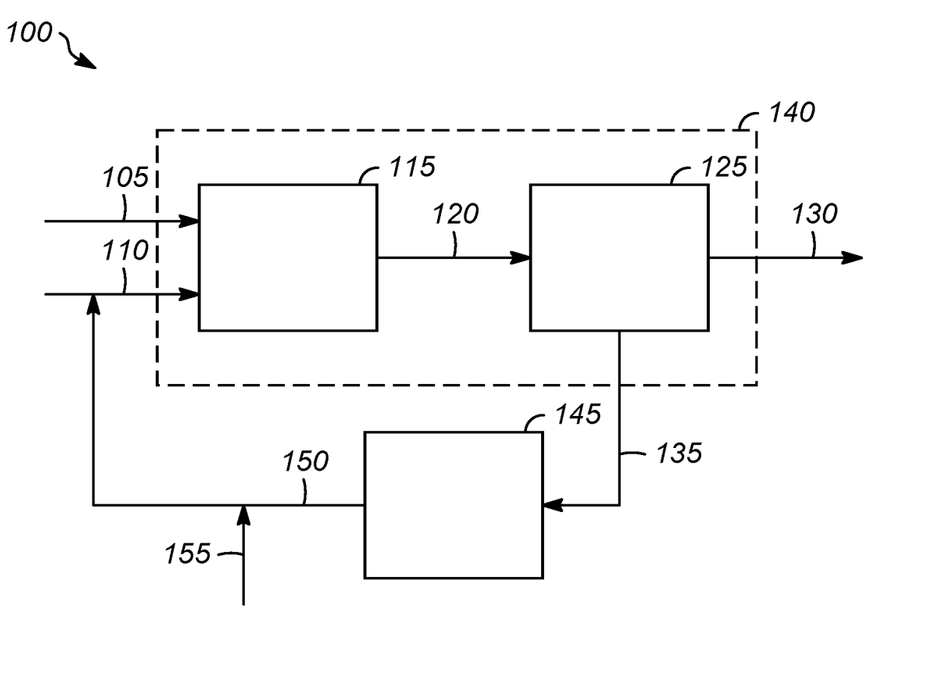
The FIGURE illustrates one embodiment of a hydrocarbon conversion process.

The present invention involves the use of non-cyclic amide or thioamide based ionic liquids as catalysts for hydrocarbon conversion processes, including, but not limited to, alkylation, oligomerization, isomerization, disproportionation, and reverse disproportionation.

A hydrocarbon feed is contacted with the non-cyclic amide or thioamide based ionic liquid in a reaction zone. The reaction zone is under the appropriate conditions for the particular hydrocarbon conversion involved. A mixture is formed including the reaction products, and the non-cyclic amide or thioamide based ionic liquid.

The reaction products can be separated from the non-cyclic amide or thioamide based ionic liquid catalyst, which can then be regenerated using a suitable regeneration process, as needed. The separated and/or regenerated non-cyclic amide or thioamide based ionic liquid catalyst can be recycled to the reaction zone.

The FIGURE illustrates one embodiment of a hydrocarbon conversion process 100 of the present invention. The hydrocarbon feed 105 and the non-cyclic amide or thioamide based ionic liquid 110 enter the hydrocarbon conversion zone 115. The non-cyclic amide or thioamide based ionic liquid 110 catalyzes the hydrocarbon conversion reaction. The effluent 120 from the hydrocarbon conversion zone 115 includes the reaction products of the hydrocarbon conversion reaction and the non-cyclic amide or thioamide based ionic liquid. The effluent 120 is sent to separation zone 125 where the reaction products 130 are separated from the non-cyclic amide or thioamide based ionic liquid 135. In some embodiments, the hydrocarbon conversion zone 115 and the separation zone 125 are in separate vessels. In other embodiments, they are in the same vessel 140.

The non-cyclic amide or thioamide based ionic liquid 135 can be recycled to the hydrocarbon conversion zone 115. The non-cyclic amide or thioamide based ionic liquid 135 can be sent to a regeneration zone 145 for regeneration if needed. The regenerated non-cyclic amide or thioamide based ionic liquid 150 can be reactivated with an acid 155 if needed. The regenerated non-cyclic amide or thioamide based ionic liquid 150 can be recycled to the hydrocarbon conversion zone 115.

The hydrocarbon conversion conditions depend on the particular hydrocarbon conversion process. The reaction temperature is less than about the decomposition temperature of the ionic liquid, or about 250° C. or less, or about 200° C. or less, or about 175° C. or less, or about 150° C. or less, or about 125° C. or less, or about 100° C. or less, or about 90° C. or less, or about 80° C. or less, or about 70° C. or less, or about 60° C. or less, typically in the range of about −20° C. to about 250° C. or in the range of about 0° C. to about 200° C., or about 0° C. to about 175° C., or about 0° C. to about 150° C., or about 10° C. to about 150° C., or about 25° C. to about 150° C., or about 30° C. to about 150° C., or about 40° C. to about 150° C., or about 50° C. to about 150° C., or about 55° C. to about 150° C., or about −20° C. to about 100° C., or about −20° C. to about 80° C., or about 0° C. to about 80° C., or about 20° C. to about 80° C.

The pressure is typically in the range of about −1.0 MPa to about 20.7 MPa, or about −1.0 MPa(g) to about 13.8 MPa(g), or about −1.0 MPa to about 8.1 MPa, or about −1.0 MPa to about 5 MPa, or about −1.0 MPa to about 3.5 MPa, or about −1.0 MPa to about 20.7 MPa, or about 0 MPa(g) to about 13.8 MPa(g), or about 0 MPa to about 8.1 MPa, or about 0 MPa to about 5 MPa, or about 0 MPa to about 3.5 MPa, or about 0.1 MPa to about 20.7 MPa, or about 0.1 MPa(g) to about 13.8 MPa(g), or about 0.1 MPa to about 8.1 MPa, or about 0.1 MPa to about 5 MPa, or about 0.1 MPa to about 3.5 MPa, or about 0.3 MPa to about 20.7 MPa, or about 0.3 MPa(g) to about 13.8 MPa(g), or about 0.3 MPa to about 8.1 MPa, or about 0.3 MPa to about 5 MPa, or about 0.3 MPa to about 3.5 MPa.

Most hydrocarbon conversion reactions in ionic liquids are biphasic and take place at the interface in the liquid state due to the low solubility of hydrocarbons in ionic liquids.

The reaction will proceed simply by contacting the hydrocarbon feed and the ionic liquid catalyst. In some instances, the reaction rate may be too slow to be commercially viable. When mass transfer rate is controlling, the reaction rate can be substantially increased by increasing the mixing intensity of the hydrocarbon feed and the ionic liquid catalyst. After a certain point, increasing the mixing intensity will not provide any additional benefit. Mixing intensity can be controlled using impellers, pumps, static mixers, flow configurations, and baffles, for example. Baffles help to prevent a vortex from forming in the reactor, which would reduce the amount of mixing.

The contacting step may be practiced in laboratory scale experiments through full scale commercial operations. The process may be operated in batch, continuous, or semi-continuous mode. The contacting step can take place in various ways, with both countercurrent and co-current flow processes being suitable.

The reaction time is a function of the degree of mixing, the reaction temperature, and the mass/volume ratio of ionic liquid catalyst to hydrocarbon being reacted. Generally, increasing any of these conditions will increase the reaction rate.

The non-cyclic amide or thioamide based ionic liquid comprises a cation and an anion and has the general formula:

wherein $R_1$, $R_2$, and $R_3$ are independently selected from hydrogen, halide, a $C_1$-$C_{12}$ alkyl group, a $C_1$-$C_{12}$ alkenyl group, a $C_4$-$C_{12}$ cycloalkyl group, a $C_4$-$C_{12}$ cycloalkenyl group, an aryl group, a substituted $C_1$-$C_{12}$ alkyl group, a substituted $C_1$-$C_{12}$ alkenyl group, a substituted $C_4$-$C_{12}$ cycloalkyl group, a substituted $C_4$-$C_{12}$ cycloalkenyl group, a substituted $C_6$-$C_{18}$ aryl group, a $C_2$-$C_{12}$ ether group, or a silyl group; or wherein $R_1$ is selected from hydrogen, halide, a $C_1$-$C_{12}$ alkyl group, a $C_1$-$C_{12}$ alkenyl group, a $C_4$-$C_{12}$ cycloalkyl group, a $C_4$-$C_{12}$ cycloalkenyl group, an aryl group, a substituted $C_1$-$C_{12}$ alkyl group, a substituted $C_1$-$C_{12}$ alkenyl group, a substituted $C_4$-$C_{12}$ cycloalkyl group, a substituted $C_4$-$C_{12}$ cycloalkenyl group, a substituted $C_6$-$C_{18}$ aryl group, a $C_2$-$C_{12}$ ether group, or a silyl group, and $R_2$ and $R_3$ form a $C_4$-$C_{12}$ cycloalkyl group, a $C_4$-$C_{12}$ cycloalkenyl group, a substituted $C_4$-$C_{12}$ cycloalkyl group, or a substituted $C_4$-$C_{12}$ cycloalkenyl group; and $X^-$ is the anion.

By substituted, we mean that the alkyl group, alkenyl group, etc. includes a group including, but not limited to, a halide, such as chloride, bromide, iodide, or fluoride, a $C_2$-$C_{12}$ ether group, a silyl group, a hydroxyl group, a thiol group, a cyano group, a sulfonyl group, an amine group, a nitrile group, a thiocyanate group, or combinations thereof.

Another way to represent

We intend both representations to be covered by the first structure.

Another way to represent

We intend both representations to be covered by the first structure.

Suitable anions include, but are not limited to carboxylates, nitrates, phosphates, phosphinates, phosphonates, imides, cyanates, borates, sulfates (including bisulfates), sulfonates (including fluoroalkanesulfonates), acetates, halides, halometallates, and combinations thereof. Examples of $X^-$ groups include, but are not limited to, tetrafluoroborate, triflate, trifluoroacetate, chloroacetate, nitrate, hydrogen sulfate, hydrogen phosphate, dicyanoimide, methylsulfonate, and combinations thereof.

In some embodiments, $X^-$ is a halide, such as chloride, bromide, iodide, or fluoride. In some embodiments, when $X^-$ is a halide, the mol ratio of cation to anion is about 1:1.

In other embodiments, $X^-$ is a halometallate. In some embodiments, the metal in the halometallate comprises Sn, Al, Zn, Mn, Fe, Ga, Cu, Ni, Co, In, or combinations thereof. In some embodiments, the halide in the halometallate comprises bromide, chloride, iodide, fluoride, or combinations thereof. One or more of the halides (but not all) can be substituted with an —OH group, for example, $Al_3Cl_9OH$. Suitable halometallates include, but are not limited to, $AlCl_4^-$, $Al_2Cl_7^-$, $Al_3Cl_{10}^-$, $AlCl_3Br^-$, $Al_2Cl_6Br^-$, $Al_3Cl_9Br^-$, $AlBr_4^-$, $Al_2Br_7^-$, $Al_3Br_{10}^-$, $GaCl_4^-$, $Ga_2Cl_7^-$, $Ga_3Cl_{10}^-$, $GaCl_3Br^-$, $Ga_2Cl_6Br^-$, $Ga_3Cl_9Br^-$, $CuCl_2^-$, $Cu_2Cl_3^-$, $Cu_3Cl_4^-$, $ZnCl_3$, $FeCl_3$, $FeCl_4$, $Fe_3Cl_7^-$, $InCl_4^-$, $InCl_5^{2-}$, $InCl_6^{3-}$, or combinations thereof. In some embodiments, when $X^-$ is the halometallate, the mol fraction of metal in the halometallate is in the range of about 0.25 to about 1.

Suitable cations include, but are not limited to, N,N-dimethylacetamidium, acetamidium, carbonyl diamidium, thioamidium, N-methylthioacetamidium, N,N-dimethylthioacetamidium, N-methylacetamidium, N,N-dimethylformamidium, benzamidium, N-methylbenzamidium, N,N-dimethylbenzamidium, or dichloroacetamidium.

Suitable non-cyclic amide or thioamide based ionic liquids include, but are not limited to, N,N-dimethylacetamidium chloride, N,N-dimethylacetamidium bromide, N,N-dimethylacetamidium $ACl_4$, N,N-dimethylacetamidium $Al_2Cl_7$, acetamidium chloride, acetamidium bromide, acetamidium $ACl_4$, acetamidium $Al_2Cl_7$, urea chloride, urea bromide, urea $ACl_4$, urea $Al_2Cl_7$, thioacetamidium chloride, thioacetamidium bromide, thioacetamidium $ACl_4$, thioacetamidium $Al_2Cl_7$, N-methylthioacetamidium chloride, N-methylthioacetamidium bromide, N-methylthioacetamidium $ACl_4$, N-methylthioacetamidium $Al_2Cl_7$, N,N-dimethylthioacetamidium chloride, N,N-dimethylthioacetamidium bromide, N,N-dimethylthioacetamidium $ACl_4$, N,N-dimethylthioacetamidium $Al_2Cl_7$, N-methylacetamidium chloride, N-methylacetamidium bromide, N-methylacetamide $ACl_4$, N-methylacetamidium $Al_2Cl_7$, N,N-dimethylformamidium chloride, N,N-dimethylformamidium bromide, N,N-dimethylformamidium $AlCl_4$, or N,N-dimethylformamidium $Al_2Cl_7$.

The non-cyclic amide or thioamide based ionic liquids can be made by reacting a non-cyclic amide or thioamide having a general formula:

with a Brnsted acid HX to form an amidium or thioamidium reaction product;

wherein $R_1$, $R_2$, and $R_3$ are independently selected from hydrogen, halide, a $C_1$-$C_{12}$ alkyl group, a $C_1$-$C_{12}$ alkenyl group, a $C_4$-$C_{12}$ cycloalkyl group, a $C_4$-$C_{12}$ cycloalkenyl group, an aryl group, a substituted $C_1$-$C_{12}$ alkyl group, a substituted $C_1$-$C_{12}$ alkenyl group, a substituted $C_4$-$C_{12}$ cycloalkyl group, a substituted $C_4$-$C_{12}$ cycloalkenyl group, a substituted $C_6$-$C_{18}$ aryl group, a $C_2$-$C_{12}$ ether group, or a silyl group; or wherein $R_1$ is selected from hydrogen, halide, a $C_1$-$C_{12}$ alkyl group, a $C_1$-$C_{12}$ alkenyl group, a $C_4$-$C_{12}$ cycloalkyl group, a $C_4$-$C_{12}$ cycloalkenyl group, an aryl group, a substituted $C_1$-$C_{12}$ alkyl group, a substituted $C_1$-$C_{12}$ alkenyl group, a substituted $C_4$-$C_{12}$ cycloalkyl group, a substituted $C_4$-$C_{12}$ cycloalkenyl group, a substituted $C_6$-$C_{18}$ aryl group, a $C_2$-$C_{12}$ ether group, or a silyl group, and $R_2$ and $R_3$ form a $C_4$-$C_{12}$ cycloalkyl group, a $C_4$-$C_{12}$ cycloalkenyl group, a substituted $C_4$-$C_{12}$ cycloalkyl group, or a substituted $C_4$-$C_{12}$ cycloalkenyl group.

In some embodiments, the non-cyclic amide or thioamide comprises N,N-dimethylacetamide, acetamide, urea, thioacetamide, N-methylthioacetamide, N,N-dimethylthioacetamide, N-methylacetamide, N,N-dimethylformamide, benzamide, N-methylbenzamide, N,N-dimethylbenzamide, or dichloroacetamide.

In some embodiments, the Brnsted acid HX is at least one of hydrochloric acid, hydrobromic acid, hydroiodic acid, sulfuric acid, nitric acid, phosphoric acid, tetrafluoroboric acid, sulfonic acid, triflic acid, toluenesulfonic acid dihaloacetic acid, and trihaloacetic acid.

The mol ratio of the non-cyclic amide or thioamide to the Brnsted acid HX is typically about 1:1.

The non-cyclic amide or thioamide is reacted with the Brnsted acid HX with or without a solvent. Suitable solvents include, but are not limited to, water, alcohols, such as methanol or ethanol, dichloromethane, chloroform, or toluene.

The reaction can be performed at room temperature and atmospheric pressure. Higher or lower temperatures and/or pressures could be used, if desired.

The reaction time to form the non-cyclic amidium or thioamidium reaction product is generally in the range of about 1 min to about 1 hr.

In some embodiments, the anion is a halide, and the non-cyclic amidium or thioamidium reaction product is a non-cyclic amidium or thioamidium halide reaction product. In some embodiments, the non-cyclic amidium or thioamidium halide reaction product is reacted with a metal halide to form an amidium halometallate reaction product.

In some embodiments, the mol ratio of the cation to the metal in the halometallate or of the amidium or thioamidium halide reaction product to the metal halide is typically in a range of about 1:0.8 to about 1:2.2, or about 1:1 to about 1:2.2, or in about 1:1.2 to about 1:2.2, or 1:1.4 to about 1:2.2, or about 1:1.16 to about 1:2.2. The ratio may be affected by the specific cation used and the synthesis temperature.

In some embodiments, the metal of the metal halide comprises Sn, Al, Zn, Mn, Fe, Ga, Cu, Ni, Co, In, or combinations thereof. Suitable metal halides include, but are not limited to, $AlCl_3$, $AlCl_2Br$, $AlBr_3$, $GaCl_3$, $GaCl_2Br$, $CuCl_3$, $FeCl_3$, or $InCl_3$. In some embodiments, one or more (but not all) of the halide can be substituted with an —OH group.

The amidium or thioamidium halide reaction product can be reacted with the metal halide in the presence of a solvent. Suitable solvents include, but are not limited to, dichloromethane, chloroform, toluene, or benzene. Protic solvents are not desirable for this reaction because they could react with the metal halide.

The ratio of the metal to the halide in the halometallate is less than the ratio of metal atoms to halide atoms in the neutral metal halide. That is, the metal:halide ratio is less than 1:X, where X is the valence of the metal. For example, the ratio of metal to halide in $Al_2Cl_7$ is 2:7, whereas the ratio in $AlCl_3$ is 1:3.

The halide in the Brnsted acid HX can be the same as the halide in the metal halide, or it can be different.

The reaction of the amidium or thioamidium halide reaction product and the metal halide can be performed at room temperature and atmospheric pressure. Higher or lower temperatures and/or pressures could be used, if desired.

The reaction time to form the non-cyclic amidium or thioamidium halometallate is generally in the range of about 1 min to about 24 hr. The reaction time is affected by whether a solvent is used in the reaction, with solvents increasing the rate of reaction.

The reaction of the amidium or thioamidium halide reaction product and the metal halide typically takes place under an inert atmosphere, such as nitrogen, argon, and the like.

The reactions (non-cyclic amide or thioamide with the Brnsted acid HX and/or amidium or thioamidium halide reaction product with the metal halide) may be practiced in laboratory scale experiments through full scale commercial operations. The process may be operated in batch, continuous, or semi-continuous mode.

Non-cyclic amide and thioamide based ionic liquids and methods of making them are described in SYNTHESIS OF NON-CYCLIC AMIDE AND THIOAMIDE BASED IONIC LIQUIDS, U.S. Pat. No. 10/450,264, which is incorporated by reference herein.

Alkylation

The alkylation reaction using the non-cyclic amide or thioamide based ionic liquid is carried out at mild temperatures, and is typically a two-phase reaction. In some embodiments, cooling may be needed. If cooling is needed, it can be provided using any known methods. The catalyst effects the alkylation of the paraffin and the olefin.

Typical alkylation reaction conditions include a temperature in the range of about −20° C. to the decomposition temperature of the ionic liquid, or about −20° C. to about 100° C., or about −20° C. to about 80° C., or about 0° C. to about 80° C., or about 20° C. to about 80° C. It is preferred to have an ionic liquid that maintains its liquid state through the operating temperature range.

The pressure is typically in the range of atmospheric (0.1 MPa(g)) to about 8.0 MPa(g), or about 0.3 MPa(g) to about 2.5 MPa(g). The pressure is preferably sufficient to keep the reactants in the liquid phase.

The residence time of the reactants in the reaction zone is in the range of a few seconds to hours, or about 0.5 min to about 60 min, or about 1 min to about 60 min, or about 3 min to about 60 min.

The acidity needs to be controlled to provide for suitable alkylation conditions. This can be done with an acid or acid precursor, such as HCl, 2-chlorobutane, or tert-butyl chloride, for example. Alternatively, the excess acid could be stripped from the fresh ionic liquid with, for example, isobutane, nitrogen, or triethylsilane (TES), and the acid level could be controlled at the low level needed during the reaction. Another alternative is to reduce the pressure and add heat to remove the excess acid.

The paraffin and olefin can be introduced separately or as a mixture. The molar ratio between the paraffin and the olefin is in the range between 100:1 and 1:1, or 50:1 and 2:1, or 20:1 and 2:1.

The heat generated by the reaction can be eliminated using any of the means known to the skilled person.

At the reactor outlet, the hydrocarbon phase is separated from the ionic liquid phase by gravity settling based on density differences, or by other separation techniques known to those skilled in the art. The hydrocarbons are separated by distillation, and the starting isoparaffin which has not been converted is recycled to the reactor.

Typical alkylation conditions may include a catalyst volume in the reactor of from 1 vol % to 50 vol %, a temperature of from 0° C. to 100° C., a pressure of from 300 kPa to 2500 kPa, an isobutane to olefin molar ratio of from 2 to 20 and a residence time of 1 min to 1 hour.

The paraffin used in the alkylation process preferably comprises a paraffin having from 4 to 10 carbon atoms, or 4 to 8 carbon atoms, or 4 to 5 carbon atoms. The olefin used in the alkylation process preferably has from 2 to 10 carbon atoms, 3 to 8 carbon atoms, or 3 to 5 carbon atoms. One application of the process is to upgrade low value $C_4$ hydrocarbons to higher value alkylates.

To that extent, one specific embodiment is the alkylation of butanes with butylenes to generate $C_8$ compounds. Preferred products include trimethylpentane (TMP), and while other $C_8$ isomers are produced, one competing isomer is dimethylhexane (DMH). The quality of the product stream can be measured in the ratio of TMP to DMH, with a high ratio desired.

In another embodiment, the invention comprises passing an isoparaffin and an olefin to an alkylation reactor, where the alkylation reactor includes an ionic liquid catalyst to react the olefin with the isoparaffin to generate an alkylate. The isoparaffin has from 4 to 10 carbon atoms, and the olefin has from 2 to 10 carbon atoms.

Oligomerization

Oligomerization reaction zones in general are maintained at conditions that may vary widely. Suitable hydrocarbon feed for oligomerization reactions includes $C_2$ to $C_{23}$ olefins.

The temperature of the oligomerization reaction zones of the present invention in which an ionic liquid catalyst is used is typically about −20° C. to about 250° C., or 50° C. to about 200° C., or 50° C. to about 150° C. Pressures in the oligomerization zone using the ionic liquid catalyst will be sufficient to maintain the liquid phase in and out of the reactor, typically about 0.3 MPa(g) to about 6.9 MPa(g) (50 to 1000 psig), or about 0.3 MPa(g) to about 3.4 MPa(g) (50 to 500 psig), or about 1.4 MPa(g) to about 2.4 MPa(g) (200 to 350 psig), or about 2.4 MPa(g) to about 6.9 MPa(g) (350 to 1000 psig). Oligomerization conditions may also include a liquid hourly space velocity (LHSV) of about 0.5 to about 50 hr-1, or about 1 to about 6 hr$^1$.

Isomerization

Suitable hydrocarbon feed for isomerization reactions includes $C_4$ to $C_{23}$ paraffins.

Suitable reaction conditions include a temperature up to the decomposition temperature of the ionic liquid, typically of about 200° C. or less, or about 175° C. or less, or about 150° C. or less, or about 125° C. or less, or about 100° C. or less, or about 90° C. or less, or about 80° C. or less, or about 70° C. or less, or about 60° C. or less, or in the range of about 0° C. to about 200° C., or about 0° C. to about 175° C., or about 0° C. to about 150° C., or about 10° C. to about 150° C., or about 25° C. to about 150° C., or about 30° C. to about 150° C., or about 40° C. to about 150° C., or about 50° C. to about 150° C., or about 55° C. to about 150° C.

The pressure in the reaction zone is typically in the range of about 0 MPa(g) to about 13.8 MPa(g), or about 0 MPa(g) to about 8.1 MPa(g), or about 0 MPa(g) to about 5 MPa(g), or about 0 MPa(g) to about 3.5 MPa(g). The pressure should be sufficient to ensure that the reaction product is in a liquid state. Small amounts of vapor may also be present, but this should be minimized.

The reaction can take place in the presence of a gas. Suitable gases include, but are not limited to methane, ethane, propane, hydrogen, hydrogen chloride, nitrogen and the like.

The reaction can take place in the presence of an added acid or acid precursor. Suitable acids or acid precursors include, but are not limited to, HCl, 2-chlorobutane, or tert-butyl chloride, for example.

The residence time in the reaction zone is generally less than about 12 hr, or less than about 10 hr, or less than 7 hr, or less than 5 hr, or less than 4 hr, or less than 3 hr, or less than 2 hr, or less than 1 hr. The reaction time can be selected so that a predetermined conversion can be obtained. The reaction time is a function of the degree of mixing, the reaction temperature, the concentration of acid and the mass/volume ratio of liquid catalyst to hydrocarbon being reacted. Generally, increasing any of these conditions will increase the reaction rate.

Isomerization processes utilizing ionic liquid catalysts were described in application Ser. No. 13/931,765, entitled CATALYTIC ISOMERIZATION OF PARAFFINS USING IONIC LIQUID, filed Jun. 28, 2013; application Ser. No. 13/931,770, entitled CATALYTIC ISOMERIZATION OF HEPTANE USING IONIC LIQUID, filed Jun. 28, 2013; application Ser. No. 13/931,776, entitled CATALYTIC ISOMERIZATION OF PENTANE USING IONIC LIQUID, filed Jun. 28, 2013; each of which is incorporated herein by reference.

Disproportionation

Suitable hydrocarbon feeds for disproportionation reactions include $C_2$ to $C_{23}$ paraffins. Feeds comprising two or more paraffins are also acceptable.

Suitable reaction conditions include a temperature of about less than the decomposition temperature of the ionic liquid, or about 250° C. or less, or about 200° C. or less, or about 175° C. or less, or about 150° C. or less, or about 125° C. or less, or about 100° C. or less, or about 90° C. or less, or about 80° C. or less, or about 70° C. or less, or about 60° C. or less, or in the range of about 0° C. to about 200° C., or about 0° C. to about 175° C., or about 0° C. to about 150° C., or about 10° C. to about 150° C., or about 25° C. to about 150° C., or about 30° C. to about 150° C., or about 40° C. to about 150° C., or about 50° C. to about 150° C., or about 55° C. to about 150° C.

The pressure in the reaction zone is typically in the range of about 0 MPa to about 20.7 MPa, or about 0 MPa to about 8.1 MPa, or about 0 MPa to about 5 MPa, or about 0 MPa to about 3.5 MPa. The pressure should be sufficient to ensure that the reaction product is in a liquid state. Small amounts of vapor may also be present, but this should be minimized.

The reaction can take place in the presence of a gas. Suitable gases include, but are not limited to methane, ethane, propane, hydrogen, hydrogen chloride, nitrogen and the like.

The reaction can take place in the presence of an added acid or acid precursor. Suitable acids or acid precursors include, but are not limited to, HCl, 2-chlorobutane, or tert-butyl chloride, for example. The residence time in the reaction zone is generally less than about 12 hr, or less than about 10 hr, or less than 7 hr, or less than 5 hr, or less than 4 hr, or less than 3 hr, or less than 2 hr, or less than 1 hr. The reaction time can be selected so that a predetermined conversion can be obtained. The reaction time is a function of the degree of mixing, the reaction temperature, the concentration of acid and the mass or volume ratio of liquid catalyst to hydrocarbon being reacted. Generally, increasing any of these conditions will increase the reaction rate.

Disproportionation processes using ionic liquids were described in application Ser. No. 13/931,780, entitled CATALYTIC DISPROPORTIONATION OF PARAFFINS USING IONIC LIQUID, filed Jun. 28, 2013; application Ser. No. 13/931,783, entitled CATALYTIC DISPROPORTIONATION OF HEPTANE USING IONIC LIQUID, filed Jun. 28, 2013; and application Ser. No. 13/931,789, entitled CATALYTIC DISPROPORTIONATION OF PENTANE USING IONIC LIQUID, filed Jun. 28, 2013; each of which is incorporated herein by reference.

Reverse Disproportionation

The microscopic reverse of pentane disproportionation is the combination of one mole of hexane and one mole of butane to form two moles of pentane. This type of reaction is referred to herein as reverse disproportionation. Reverse disproportionation-type reactions can occur in which two paraffins having different carbon numbers react to form two different paraffins having different carbon numbers from those of the feed where the total number of moles of product and moles of carbon and hydrogen in the products does not change from the total number in the feed (e.g., pentane and octane reacting to form hexane and heptane). Utilizing the equilibrium among the various species, the concentration of the product can be controlled by varying the relative ratios of the species. Consequently, two different paraffinic feed sources of varying carbon count can be reacted to obtain a product containing paraffins of intermediate carbon count.

More generally, this process involves the net transfer of $CH_2$ units between paraffins, where $CH_2$ unit refers to the transfer of 1 C and 2 H, not necessarily a methylene unit. The products result from the donation and acceptance of net $CH_2$ units to and from various paraffins. Thus, two paraffinic feeds having different carbon counts can be reacted to produce a product having an intermediate carbon count. For example, the reaction of butane with a larger paraffin, e.g., $C_{16}$, produces a product containing paraffins in the $C_5$ to $C_{15}$ range.

In addition to the net $CH_2$ transfer, the process favors the formation of branched paraffins, which are more valuable than normal paraffins because they have more desirable octane numbers and cloud points.

Typically, hydrocarbons having a carbon number from 1-200 or more can be selected as feeds for the process. Depending on the desired product, one or two (or more) hydrocarbon feeds could be selected.

In some embodiments involving reverse disproportion, one larger and one smaller paraffin feed can be used to produce a product composition having an intermediate carbon count. The smaller feed typically has carbon numbers ranging from 1-198, and the larger feed typically has carbon numbers ranging from 3-200. There is generally a difference of at least 2 or more carbon numbers between the two feeds, or at least 3, or at least 4, or at least 5, or at least 6 or more. In some embodiments involving reverse disproportionation, the reaction mixture has an amount of at least one of the intermediate products equal to or in excess of the amount formed by the disproportionation reaction of either feed alone.

In some embodiments, the smaller feed typically has carbon numbers ranging from 4-23, and the larger feed typically has carbon numbers ranging from 6-25. There is generally a difference of at least 2 or more carbon numbers between the two feeds, or at least 3, or at least 4, or at least 5, or at least 6 or more.

The liquid hydrocarbon feed is contacted with the liquid catalyst at temperatures of in the range of about −20° C. to the decomposition temperature of the ionic liquid, or about 250° C. or less, or about 200° C. or less, or about 175° C. or less, or about 150° C. or less, or about 125° C. or less, or about 100° C. or less, or about 90° C. or less, or about 80° C. or less, or about 70° C. or less, or about 60° C. or less, or in the range of about 0° C. to about 200° C., or about 0° C. to about 175° C., or about 0° C. to about 150° C., or about 10° C. to about 150° C., or about 25° C. to about 150° C., or about 30° C. to about 150° C., or about 40° C. to about 150° C., or about 50° C. to about 150° C., or about 55° C. to about 150° C.

The pressure in the reaction zone is typically in the range of about 0 MPa to about 20.7 MPa, or about 0 MPa to about 8.1 MPa. In some embodiments, the pressure should be sufficient to ensure that the hydrocarbon feed is in a liquid state. Small amounts of vapor may also be present, but this should be minimized. In other embodiments, using propane and other light paraffins, the temperatures may not allow for a liquid state. In this case, a gas phase or a supercritical phase can be used. The reaction typically takes places in the presence of a gas. Suitable gases include, but are not limited to nitrogen, hydrogen, argon, helium, hydrogen chloride and the like.

The reaction can take place in the presence of an added acid or acid precursor. Suitable acids or acid precursors include, but are not limited to, HCl, 2-chlorobutane, or tert-butyl chloride, for example.

The residence time in the reaction zone is generally less than about 10 hr, or less than 7 hr, or less than 5 hr, or less than 4 hr, or less than 3 hr, or less than 2 hr, or less than 1 hr.

The reaction time is a function of the degree of mixing, the reaction temperature, the concentration of acid and the mass/volume ratio of liquid catalyst to hydrocarbon being reacted. Generally, increasing any of these conditions will increase the reaction rate.

Reverse disproportionation processes using ionic liquids were described in Application Ser. No. 61/841,263, entitled CATALYTIC REVERSE DISPROPORTIONATION OF PARAFFINS USING IONIC LIQUID, filed Jun. 28, 2013, and application Ser. No. 14/303,586, entitled CATALYTIC REVERSE DISPROPORTIONATION OF PARAFFINS USING IONIC LIQUID, filed Jun. 12, 2014, each of which is incorporated herein by reference.

EXAMPLES

Example 1: Synthesis of N,N-Dimethylacetamidium Chloride

An HCl in ethanol solution (1.25M, 35 mL, 43.8 mmol) was added to N,N-dimethylacetamide (3.55 g, 40.2 mmol) at room temperature. After stirring for 1 h, the volatiles were removed at 50° C. under reduced pressure to yield a white solid. Yield: 4.87 g, 98%. $^1$H NMR (500 MHz, $CDCl_3$): 2.51 (s, 3H), 3.14 (s, 6H), 15.58 (s, 1H). $^{13}$C NMR (125 MHz, $CDCl_3$): 18.19, 38.67, 174.83.

Example 1: Synthesis of N,N-Dimethylacetamidium Chloroaluminate

Under a nitrogen atmosphere, aluminum trichloride was slowly added to N,N-dimethylacetamidium chloride. Upon addition of the aluminum chloride with stirring, the mixture began to liquefy. The mixture was stirred 1.67 h with stirring until the material was completely liquefied. Yield: 11.2 g, 90.3%. $^1$H NMR (500 MHz, $CDCl_3$): 2.55 (s, 3H), 3.34 (d, 6H). $^{13}$C NMR (125 MHz, $CDCl_3$): 21.27, 39.39, 40.77, 173.02.

Example 1: Alkylation Experiment

In a nitrogen atmosphere, N,N-dimethylacetamidium chloroaluminate was loaded into a 300 ml autoclave containing a baffle. Prior to loading, the autoclave and baffle had been dried for several hours above 100° C. The number of acid sites in the ionic liquid was adjusted to optimize the performance by addition of 2-chlorobutane. (The number of acid sites could be adjusted by changing the catalyst loading or by changing the amount of acid or acid precursor added.) The autoclave was charged with 80 g isobutane and pressurized with 3.4 MPa(g) (500 psig) of nitrogen. The contents were stirred at 1600 rpm, and 8 g 2-butene was added over time (about 118.72 mL/h) at room temperature. After 8 min, the reaction mixture was allowed to settle and the liquid product was sampled directly from the autoclave. The sample was passed through a silica column then analyzed by gas chromatography. The results are shown Table 1.

The groupings below include all isomers having the same carbon number. The % butenes conversion was calculated using 100−(the weight of butenes in the product divided by the weight of butenes added). RONC is the Research Octane Number Calculated. TMP/DMH is the weight ratio of trimethylpentanes to dimethylhexanes in the product. The % Selectivity is (wt % of that paraffin)/(sum of wt % of the $C_5$ and larger products formed). The yield is (the mass of $C_5$ and larger products formed)/(the mass of the $C_4$ olefin added).

TABLE 1

|  | 3.8 g N,N-dimethylacetamidium chloroaluminate + 0.466 g 2-chlorobutane |
| --- | --- |
| Mol ratio cation:mol Al:chlorobutane | 1:1.8:0.4 |
| Vol % IL | 1.9 |
| Reaction Time | 8 min |
| i/o (mol ratio) | 7.9 |
| Butenes Conversion (%) | 95.2 |
| RONC | 95.0 |
| % Sel C8 | 73.7 |
| % Sel C9 | 11.6 |
| % Sel C5-7 | 14.7 |
| TMP/DMH | 13.9 |
| Yield (C5+/C4=) | 2.19 |

By the term "about," we mean within 10% of the value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

Specific Embodiments

While the following is described in conjunction with specific embodiments, it will be understood that this description is intended to illustrate and not limit the scope of the preceding description and the appended claims.

A first embodiment of the invention is a process comprising contacting a hydrocarbon feed with a non-cyclic amide or thioamide based ionic liquid catalyst in a hydrocarbon conversion zone under hydrocarbon conversion conditions to form a mixture comprising reaction products, and the non-cyclic amide or thioamide based ionic liquid catalyst. An embodiment of the invention is one, any or all of prior embodiments in this paragraph up through the first embodiment in this paragraph wherein the non-cyclic amide or thioamide based ionic liquid catalyst comprises a cation and an anion, and wherein the ionic liquid has a formula wherein $R_1$, $R_2$, and $R_3$ are independently selected from hydrogen, halide, a $C_1$-$C_{12}$ alkyl group, a $C_1$-$C_{12}$ alkenyl group, a $C_4$-$C_{12}$ cycloalkyl group, a $C_4$-$C_{12}$ cycloalkenyl group, an aryl group, a substituted $C_1$-$C_{12}$ alkyl group, a substituted $C_1$-$C_{12}$ alkenyl group, a substituted $C_4$-$C_{12}$ cycloalkyl group, a substituted $C_4$-$C_{12}$ cycloalkenyl group, a substituted $C_6$-$C_{18}$ aryl group, a $C_2$-$C_{12}$ ether group, or a silyl group; or wherein $R_1$ is selected from hydrogen, halide, a $C_1$-$C_{12}$ alkyl group, a $C_1$-$C_{12}$ alkenyl group, a $C_4$-$C_{12}$ cycloalkyl group, a $C_4$-$C_{12}$ cycloalkenyl group, an aryl group, a substituted $C_1$-$C_{12}$ alkyl group, a substituted $C_1$-$C_{12}$ alkenyl group, a substituted $C_4$-$C_{12}$ cycloalkyl group, a substituted $C_4$-$C_{12}$ cycloalkenyl group, a substituted $C_6$-$C_{18}$ aryl group, a $C_2$-$C_{12}$ ether group, or a silyl group, and $R_2$ and $R_3$ form a $C_4$-$C_{12}$ cycloalkyl group, a $C_4$-$C_{12}$ cycloalkenyl group, a substituted $C_4$-$C_{12}$ cycloalkyl group, or a substituted $C_4$-$C_{12}$ cycloalkenyl group; and $X^-$ is an anion. An embodiment of the invention is one, any or all of prior embodiments in this paragraph up through the first embodiment in this paragraph wherein the anion is a carboxylate, a nitrate, a phosphate, a phosphinate, a phosphonate, an imide, a cyanate, a borate, a sulfate, a sulfonate, an acetate, a halide, a halometallate, and combinations thereof An embodiment of the invention is one, any or all of prior embodiments in this paragraph up through the first embodiment in this paragraph wherein the anion is the halometallate, wherein the metal in the halometallate comprises Sn, Al, Zn, Mn, Fe, Ga, Cu, Ni, Co, In, or combinations thereof, and wherein the halide in the halometallate comprises bromide, chloride, iodide, fluoride, or combinations thereof, and wherein the halometallate optionally includes an —OH group. An embodiment of the invention is one, any or all of prior embodiments in this paragraph up through the first embodiment in this paragraph wherein the anion is the halometallate, and wherein the halometallate comprises $AlCl_4^-$, $Al_2Cl_7^-$, $Al_3Cl_{10}^-$, $AlCl_3Br^-$, $Al_2Cl_6Br^-$, $Al_3Cl_9Br^-$, $AlBr_4^-$, $Al_2Br_7^-$, $Al_3Br_{10}^-$, $GaCl_4^-$, $Ga_2Cl_7^-$, $Ga_3Cl_{10}^-$, $GaCl_3Br^-$, $Ga_2Cl_6Br^-$, $Ga_3Cl_9Br^-$, $CuCl_2^-$, $Cu_2Cl_3^-$, $Cu_3Cl_4^-$, $ZnCl_3^-$, $FeCl_3^-$, $FeCl_4^-$, $Fe_3Cl_7^-$, $InCl_4^-$, $InCl_5^{2-}$, $InCl_6^{3-}$, or combinations thereof. An embodiment of the invention is one, any or all of prior embodiments in this paragraph up through the first embodiment in this paragraph wherein the cation comprises N,N-dimethylacetamidium, acetamidium, carbonyl diamidium, thioamidium, N-methylthioacetamidium, N,N-dimethylthioacetamidium, N-methylacetamidium, N,N-dimethylformamidium, benzamidium, N-methylbenzamidium, N,N-dimethylbenzamidium, or dichloroacetamidium. An embodiment of the invention is one, any or all of prior embodiments in this paragraph up through the first embodiment in this paragraph wherein the non-cyclic amide or thioamide based ionic liquid is N,N-dimethylacet- amidium chloride, N,N-dimethylacetamidium bromide, N,N-dimethylacetamidium $ACl_4$, N,N-dimethylacetamidium $Al_2Cl_7$, acetamidium chloride, acetamidium bromide, acetamidium $ACl_4$, acetamidium $Al_2Cl_7$, urea chloride, urea bromide, urea $ACl_4$, urea $Al_2Cl_7$, thioacetamidium chloride, thioacetamidium bromide, thioacetamidium $ACl_4$, thioacetamidium $Al_2Cl_7$, N-methylthioacetamidium chloride, N-methylthioacetamidium bromide, N-methylthioacetamidium $ACl_4$, N-methylthioacetamidium $Al_2Cl_7$, N,N-dimethylthioacetamidium chloride, N,N-dimethylthioacetamidium bromide, N,N-dimethylthioacetamidium $ACl_4$, N,N-dimethylthioacetamidium $Al_2Cl_7$, N-methylacetamidium chloride, N-methylacetamidium bromide, N-methylacetamide $ACl_4$, N-methylacetamidium $Al_2Cl_7$, N,N-dimethylformamidium chloride, N,N-dimethylformamidium bromide, N,N-dimethylformamidium $ACl_4$, or N,N-dimethylformamidium $Al_2Cl_7$. An embodiment of the invention is one, any or all of prior embodiments in this paragraph up through the first embodiment in this paragraph wherein the hydrocarbon conversion process comprises at least one of alkylation, oligomerization, isomerization, disproportionation, and reverse disproportionation. In embodiment of the invention is one, any or all of prior embodiments in this paragraph up through the first embodiment in this paragraph wherein the anion is the halometallate and wherein a mol ratio of the cation to the metal in the halometallate is in a range of about 10.8 to about 12.2. In embodiment of the invention is one, any or all of prior embodiments in this paragraph up through the first embodiment in this paragraph wherein the anion is the halometallate and wherein a ratio of metal to halide in the halometallate is less than a ratio of metal to halide in a neutral metal halide. An embodiment of the invention is one, any or all of prior embodiments in this paragraph up through the first embodiment in this paragraph wherein the hydrocarbon conversion conditions include at least one of a temperature in a range of about −20° C. to about 250° C., and a pressure in a range of about −1.0 MPa(g) to about 20.7 MPa(g). An embodiment of the invention is one, any or all of prior embodiments in this paragraph up through the first embodiment in this paragraph further comprising separating the reaction products from the non-cyclic amide or thioamide based ionic liquid catalyst. An embodiment of the invention is one, any or all of prior embodiments in this paragraph up through the first embodiment in this paragraph further comprising regenerating the non-cyclic amide or thioamide based ionic liquid catalyst, and recycling the regenerated non-cyclic amide or thioamide based ionic liquid to the hydrocarbon conversion zone. An embodiment of the invention is one, any or all of prior embodiments in this paragraph up through the first embodiment in this paragraph further comprising adding an acid, or an acid precursor to the hydrocarbon conversion zone. An embodiment of the invention is one, any or all of prior embodiments in this paragraph up through the first embodiment in this paragraph wherein the non-cyclic amide or thioamide based ionic liquid is present in an amount of about 1 vol % to about 75 vol % of the total volume of material in the hydrocarbon conversion zone. An embodiment of the invention is one, any or all of prior embodiments in this paragraph up through the first embodiment in this paragraph wherein the substituted $C_1$-$C_{12}$ alkyl group, the substituted $C_1$-$C_{12}$ alkenyl group, the substituted $C_4$-$C_{12}$ cycloalkyl group, the substituted $C_4$-$C_{12}$ cycloalkenyl group, or the substituted aryl group is substituted with a halide, a $C_2$-$C_{12}$ ether group, a silyl group, a hydroxyl group, a thiol group, a cyano group, a sulfonyl group, an amine group, a nitrile group, a thiocyanate group, or combinations thereof. An embodiment of the invention is one, any or all of prior embodiments in this paragraph up through the first embodiment in this paragraph wherein the hydrocarbon conversion process comprises alkylation, the feed comprises $C_2$ to $C_{10}$ paraffins and olefins, and wherein the hydrocarbon conversion conditions include a temperature of from about −20° C. to about 100° C., a pressure from about 0.3 MPa(g) to about 2.5 MPa(g), an isobutane to olefin molar ratio from about 2 to about 20, and a residence time of about 1 min to about 1 hour. An embodiment of the invention is one, any or all of prior embodiments in this paragraph up through the first embodiment in this paragraph wherein the hydrocarbon conversion process comprises oligomerization, the feed comprises $C_2$ to $C_{23}$ olefins, and wherein the hydrocarbon conversion conditions include a temperature of about 50° C. to about 200° C., a pressure of about 0.3 MPa(g) to about 3.4 MPa(g), and a liquid hourly space velocity of about 0.5 to about 50 hr-1. An embodiment of the invention is one, any or all of prior embodiments in this paragraph up through the first embodiment in this paragraph wherein the hydrocarbon conversion process comprises at least one of isomerization, and disproportionation, the feed comprises $C_2$ to $C_{23}$ paraffins, and wherein the hydrocarbon conversion conditions include a temperature of about 0° C. to about 200° C., a pressure of about 0 MPa(g) to about 20.7 MPa(g), and a residence time of less than about 18 hour. An embodiment of the invention is one, any or all of prior embodiments in this paragraph up through the first embodiment in this paragraph wherein the hydrocarbon conversion process comprises reverse disproportionation, the feed comprises $C_4$ to $C_{25}$ paraffins, and wherein the hydrocarbon conversion conditions include a temperature of about 0° C. to about 250° C., a pressure of about 0 MPa(g) to about 20.7 MPa(g), and a residence time of less than about 18 hour.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A hydrocarbon conversion process comprising:
 contacting a hydrocarbon feed with a non-cyclic amide or thioamide based ionic liquid catalyst in a hydrocarbon conversion zone under hydrocarbon conversion conditions to form a mixture comprising reaction products and the non-cyclic amide or thioamide based ionic liquid catalyst;
 wherein the non-cyclic amide or thioamide based ionic liquid catalyst comprises a cation and an anion, and wherein the ionic liquid has a formula:

wherein $R_1$, $R_2$, and $R_3$ are independently selected from hydrogen, halide, a $C_1$-$C_{12}$ alkyl group, a $C_1$-$C_{12}$ alkenyl group, a $C_4$-$C_{12}$ cycloalkyl group, a $C_4$-$C_{12}$ cycloalkenyl group, an aryl group, a substituted $C_1$-$C_{12}$ alkyl group, a substituted $C_1$-$C_{12}$ alkenyl group, a substituted $C_4$-$C_{12}$ cycloalkyl group, a substituted $C_4$-$C_{12}$ cycloalkenyl group, a substituted $C_6$-$C_{18}$ aryl group, a $C_2$-$C_{12}$ ether group, or a silyl group; or wherein $R_1$ is selected from hydrogen, halide, a $C_1$-$C_{12}$ alkyl group, a $C_1$-$C_{12}$ alkenyl group, a $C_4$-$C_{12}$ cycloalkyl group, a $C_4$-$C_{12}$ cycloalkenyl group, an aryl group, a substituted $C_1$-$C_{12}$ alkyl group, a substituted $C_1$-$C_{12}$ alkenyl group, a substituted $C_4$-$C_{12}$ cycloalkyl group, a substituted $C_4$-$C_{12}$ cycloalkenyl group, a substituted $C_6$-$C_{18}$ aryl group, a $C_2$-$C_{12}$ ether group, or a silyl group, and $R_2$ and $R_3$ form a $C_4$-$C_{12}$ cycloalkyl group, a $C_4$-$C_{12}$ cycloalkenyl group, a substituted $C_4$-$C_{12}$ cycloalkyl group, or a substituted $C_4$-$C_{12}$ cycloalkenyl group; and $X^-$ is an anion.

2. The process of claim 1, wherein the anion is a carboxylate, a nitrate, a phosphate, a phosphinate, a phosphonate, an imide, a cyanate, a borate, a sulfate, a sulfonate, an acetate, a halide, a halometallate, or combinations thereof.

3. The process of claim 2, wherein the anion is the halometallate, wherein the metal in the halometallate comprises Sn, Al, Zn, Mn, Fe, Ga, Cu, Ni, Co, In, or combinations thereof, and wherein the halide in the halometallate comprises bromide, chloride, iodide, fluoride, or combinations thereof, and wherein the halometallate optionally includes an —OH group.

4. The process of claim 2, wherein the anion is the halometallate, and wherein the halometallate comprises $AlCl_4^-$, $Al_2Cl_7^-$, $Al_3Cl_{10}^-$, $AlCl_3Br^-$, $Al_2Cl_6Br^-$, $Al_3Cl_9Br^-$, $AlBr_4^-$, $Al_2Br_7^-$, $Al_3Br_{10}^-$, $GaCl_4^-$, $Ga_2Cl_7^-$, $Ga_3Cl_{10}^-$, $GaCl_3Br^-$, $Ga_2Cl_6Br^-$, $Ga_3Cl_9Br^-$, $CuCl_2^-$, $Cu_2Cl_3^-$, $Cu_3Cl_4^-$, $ZnCl_3^-$, $FeCl_3^-$, $FeCl_4^-$, $Fe_3Cl_7^-$, $InCl_4^-$, $InCl_5^{2-}$, $InCl_6^{3-}$, or combinations thereof.

5. The process of claim 2, wherein the cation comprises N,N-dimethylacetamidium, acetamidium, carbonyl diamidium, thioamidium, N-methylthioacetamidium, N,N-dimethylthioacetamidium, N-methylacetamidium, N,N-dimethylformamidium, benzamidium, N-methylbenzamidium, N,N-dimethylbenzamidium, or dichloroacetamidium.

6. The process of claim 1, wherein the non-cyclic amide or thioamide based ionic liquid is N,N-dimethylacetamidium chloride, N,N-dimethylacetamidium bromide, N,N-dimethylacetamidium $AlCl_4$, N,N-dimethylacetamidium $Al_2Cl_7$, acetamidium chloride, acetamidium bromide, acetamidium $AlCl_4$, acetamidium $Al_2Cl_7$, urea chloride, urea bromide, urea $AlCl_4$, urea $Al_2Cl_7$, thioacetamidium chloride, thioacetamidium bromide, thioacetamidium $AlCl_4$, thioacetamidium $Al_2Cl_7$, N-methylthioacetamidium chloride, N-methylthioacetamidium bromide, N-methylthioacetamidium $AlCl_4$, N-methylthioacetamidium $Al_2Cl_7$, N,N-dimethylthioacetamidium chloride, N,N-dimethylthioacetamidium bromide, N,N-dimethylthioacetamidium $AlCl_4$, N,N-dimethylthioacetamidium $Al_2Cl_7$, N-methylacetamidium chloride, N-methylacetamidium bromide, N-methylacetamide $AlCl_4$, N-methylacetamidium $Al_2Cl_7$, N,N-dimethylformamidium chloride, N,N-dimethylformamidium bromide, N,N-dimethylformamidium $AlCl_4$, or N,N-dimethylformamidium $Al_2Cl_7$.

7. The process of claim 1, wherein the hydrocarbon conversion process comprises at least one of alkylation, oligomerization, isomerization, disproportionation, and reverse disproportionation.

8. The process of claim 2, wherein the anion is the halometallate and wherein a mol ratio of the cation to the metal in the halometallate is in a range of about 1:0.8 to about 1:2.2.

9. The process of claim 2, wherein the anion is the halometallate and wherein a ratio of metal to halide in the halometallate is less than a ratio of metal to halide in a neutral metal halide.

10. The process of claim 1, wherein the hydrocarbon conversion conditions include at least one of a temperature in a range of about −20° C. to about 250° C., and a pressure in a range of about −1.0 MPa(g) to about 20.7 MPa(g).

11. The process of claim 1, further comprising separating the reaction products from the non-cyclic amide or thioamide based ionic liquid catalyst.

12. The process of claim 1, further comprising regenerating the non-cyclic amide or thioamide based ionic liquid catalyst, and recycling the regenerated non-cyclic amide or thioamide based ionic liquid to the hydrocarbon conversion zone.

13. The process of claim 1, further comprising adding an acid or an acid precursor to the hydrocarbon conversion zone.

14. The process of claim 1, wherein the non-cyclic amide or thioamide based ionic liquid is present in an amount of about 1 vol % to about 75 vol % of the total volume of material in the hydrocarbon conversion zone.

15. The process of claim 1, wherein the substituted $C_1$-$C_{12}$ alkyl group, the substituted $C_1$-$C_{12}$ alkenyl group, the substituted $C_4$-$C_{12}$ cycloalkyl group, the substituted $C_4$-$C_{12}$ cycloalkenyl group, or the substituted aryl group is substituted with a halide, a $C_2$-$C_{12}$ ether group, a silyl group, a hydroxyl group, a thiol group, a cyano group, a sulfonyl group, an amine group, a nitrile group, a thiocyanate group, or combinations thereof.

16. The process of claim 1, wherein the hydrocarbon conversion process comprises alkylation, the feed comprises $C_4$ to $C_{10}$ isoparaffins and $C_2$ to $C_{10}$ olefins, and wherein the hydrocarbon conversion conditions include a temperature of from about −20° C. to about 100° C., a pressure from about 0.3 MPa(g) to about 2.5 MPa(g), an isoparaffin to olefin molar ratio from about 2 to about 20, and a residence time of about 1 min to about 1 hour.

17. The process of claim 1, wherein the hydrocarbon conversion process comprises oligomerization, the feed comprises $C_2$ to $C_{23}$ olefins, and wherein the hydrocarbon conversion conditions include a temperature of about 50° C. to about 200° C., a pressure of about 0.3 MPa(g) to about 3.4 MPa(g), and a liquid hourly space velocity of about 0.5 to about 50 $hr^{-1}$.

18. The process of claim 1, wherein the hydrocarbon conversion process comprises at least one of isomerization and disproportionation, the feed comprises $C_4$ to $C_{23}$ paraffins for isomerization, or $C_2$ to $C_{23}$ paraffins for disproportionation, and wherein the hydrocarbon conversion conditions include a temperature of about 0° C. to about 200° C., a pressure of about 0 MPa(g) to about 20.7 MPa(g), and a residence time of less than about 18 hour.

19. The process of claim 1, wherein the hydrocarbon conversion process comprises reverse disproportionation, the feed comprises two different paraffins in a range of $C_4$ to $C_{25}$, and wherein the hydrocarbon conversion conditions include a temperature of about 0° C. to about 250° C., a pressure of about 0 MPa(g) to about 20.7 MPa(g), and a residence time of less than about 18 hour.

* * * * *